(12) United States Patent
Logan et al.

(10) Patent No.: US 7,028,555 B1
(45) Date of Patent: Apr. 18, 2006

(54) APPARATUS AND METHOD FOR TESTING TIRE LINER SURFACE ADHESION CAPABILITY

(75) Inventors: Brian Matthew Logan, Akron, OH (US); Bruce Raymond Hahn, Hudson, OH (US); Martin Lamar Sentmanat, Akron, OH (US); Gary Edwin Tubb, Copley, OH (US); Joseph Carmine Lettieri, Stow, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 24 days.

(21) Appl. No.: 10/984,491

(22) Filed: Nov. 9, 2004

(51) Int. Cl.
*G01N 3/08* (2006.01)

(52) U.S. Cl. .................... 73/827; 73/150 A
(58) Field of Classification Search ............ 73/827, 73/150 A, 788
See application file for complete search history.

(56) References Cited

U.S. PATENT DOCUMENTS

| 5,181,975 | A | * | 1/1993 | Pollack et al. ............ 152/152.1 |
| 5,500,065 | A | * | 3/1996 | Koch et al. ................. 156/123 |
| 5,575,868 | A | * | 11/1996 | Mann ........................ 156/64 |
| 5,673,586 | A | * | 10/1997 | Mann ....................... 73/150 A |
| 5,696,327 | A | * | 12/1997 | Huang et al. ................ 73/845 |

* cited by examiner

*Primary Examiner*—Edward Lefkowitz
*Assistant Examiner*—Freddie Kirkland, III
(74) *Attorney, Agent, or Firm*—Richard B. O'Planick

(57) ABSTRACT

Apparatus and method for measuring adhesion capability in a tire liner, the apparatus including a film strip attaching to the tire liner and having a through opening and an attachment interface distanced from the opening; an adhesive backed cover member attaching to the film strip in covering relationship to the strip opening and a cover member surface portion establishing an adhesive bond with the tire liner through the film strip opening; means attached to the strip attachment interface for exerting a directional peeling force upon the strip sufficient to unitarily peel the film strip and the cover member from the tire liner; and means for measuring the directional peeling force.

10 Claims, 5 Drawing Sheets

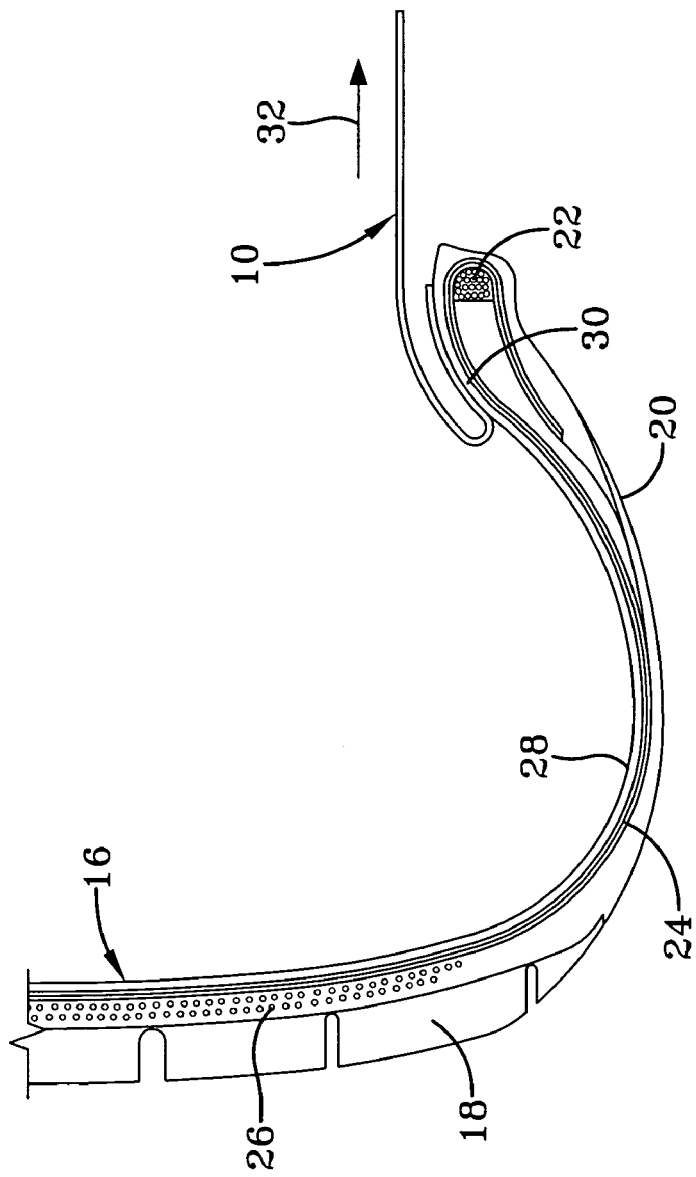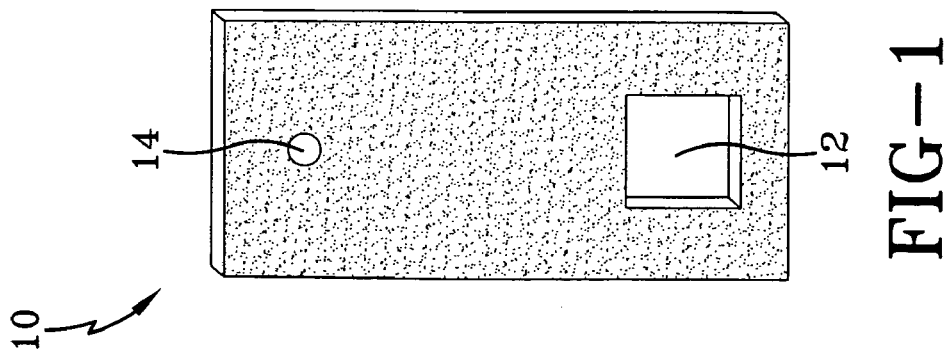

APPARATUS AND METHOD FOR TESTING TIRE LINER SURFACE ADHESION CAPABILITY

FIELD OF THE INVENTION

The invention relates generally to the attachment of tire monitoring apparatus to a tire liner for the purpose of monitoring one or more tire parameters and, more specifically, to the method and apparatus for testing tire liner surface adhesion capability in order to ensure a positive connection between the apparatus and liner

BACKGROUND OF THE INVENTION

It is common to employ apparatus, including an antenna, for electronically transmitting tire or wheel identification or other data at radio frequency. The apparatus may include a radio-frequency transponder comprising an integrated circuit chip having data capacity at least sufficient to retain identification information for the tire or wheel. Other data, such as the inflation pressure of the tire or the temperature of the tire or wheel at the transponder location, can be transmitted by the transponder along with the identification data. The apparatus may be in the form of an annular assembly or a patch and such apparatus is typically affixed to a preferred tire liner location by appropriate means such as an adhesive. Conventionally, the adhesive is applied to a target location on the tire liner and the monitoring apparatus is pressed into the adhesive. When the adhesive dries (cures) the monitoring apparatus is securely attached to the tire liner by means of the cured adhesive.

The integrity of the attachment between the monitoring apparatus and the liner is significantly a function of the "adhesion capability" of the liner which is a function of the cleanliness of the liner or some other parameter such as surface tension. An accurate measurement of adhesion capability will give an indication of how well adhesive will stick to the liner surface. Adhesion capability will vary depending on the release agent applied to the liner; the bladder pattern in the liner; and the tire manufacturer's material specifications.

There is, accordingly, need to measure adhesion capability in tire liner in an accurate and repeatable manner. Such a measurement ideally will be undertaken before the monitoring apparatus is attached in order to determine whether the apparatus will stick to the tire line surface. Measurement of adhesion capability can be used to control the installation or cleaning process and provide the means for determining whether the target liner surface displays a sufficient adhesion capability. Should the target liner surface display a less than satisfactory adhesion capability, additional cleaning or the surface may be undertaken in a timely manner or the attachment procedure (e.g. curing time) may be adjusted.

SUMMARY OF THE INVENTION

The subject invention provides apparatus and method for measuring adhesion capability between a tire liner surface and external apparatus intended for adhesive attachment thereto. In one aspect of the invention, a film is provided for application to a tire liner, the film having an opening positioned to overlap a liner target region. The film further includes an attachment interface distanced from the film opening. An adhesive backed tape is included in the apparatus for application over the film opening and into an attachment with the tire liner through the film opening. Measuring means engages the film attachment interface and effects a peeling of the tape from the liner surface while measuring the force required. The force measurement is indicative of the adhesion capability of the tire liner surface. According to another aspect of the invention, a method for deploying and utilizing the measuring apparatus is disclosed comprising the steps: positioning a film over a tire liner surface, the film having an opening disposed to overlap a liner target region and an attachment interface distanced from the film opening; applying an adhesive backed tape to the film over the film opening and into an attachment with a portion of the tire liner target region through the film opening; engaging the film through the film attachment interface to effect a peeling of the tape from the liner surface; and measuring the force required to effect the peeling of the tape from the liner surface. Pursuant to a further aspect of the invention, a tire in combination with adhesion capability measuring apparatus is disclosed.

BRIEF DESCRIPTION OF THE DRAWINGS

The invention will be described by way of example and with reference to the accompanying drawings in which:

FIG. 1 is a front perspective view of a film strip configured to the present invention;

FIG. 2 is a side sectional view of a tire portion having an adhesive capacity measuring strip affixed thereto;

DETAILED DESCRIPTION OF THE INVENTION

Figure 3:
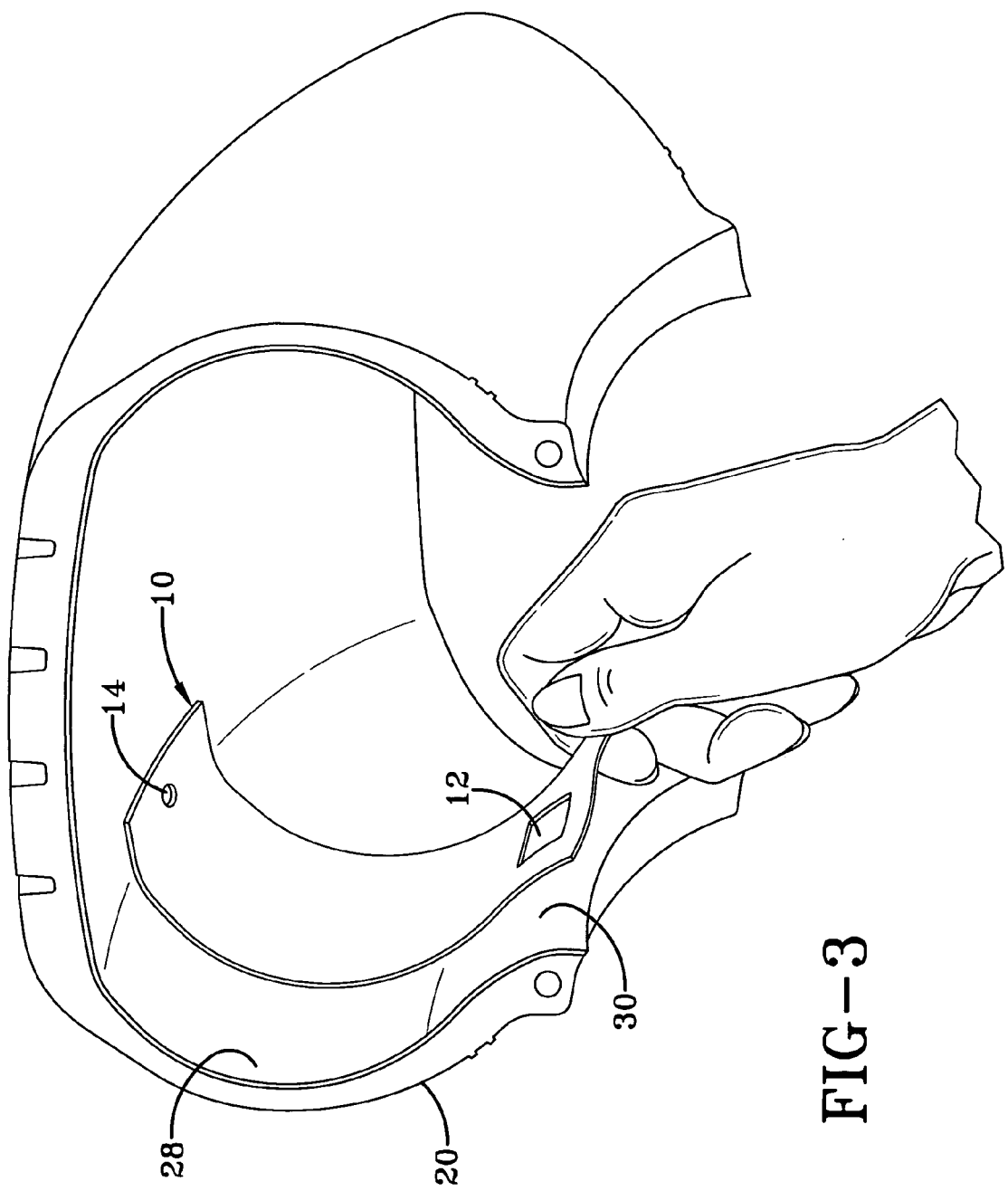
FIG. 3 is a perspective view of the placement of the film strip against the target region of a tire.

Referring initially to FIGS. 1 and 2, an apparatus for measuring adhesion capability in a tire liner surface is disclosed as including a strip of film 10 composed of Mylar or other suitable material. The film strip 10 includes a through opening 12 of generally square configuration although an opening of other shape or geometric configuration may be employed if desired. The strip 10 is of elongate rectangular shape but other shapes may also be devised and employed. Strip 10 has an attachment interface hole 14 at an end distant from the opening 12. Other means and manners of providing a mechanical connection to the strip 10 may substituted.

The subject apparatus and method is suitable for testing a tire 16 of conventional construction including a tire tread 18, sidewalls 20, a bead 22, reinforcing cords 24, and a belt structure 26 underlying the tread 18. An inner liner 28 is provided surrounding the tire air cavity and is composed of conventional fabric and rubber composites and material. The surface of liner 28 is typically treated with agents during tire formation to facilitate removal of the tire from a mold. However, the residual mold release agents present on the liner 28 may make the liner less suitable for adhesive attachment of tire monitoring apparatus thereto as will be explained below.

It is known to mount tire monitoring apparatus to the tire liner 28 for the measurement and monitoring of various tire parameters during tire usage or for the purpose of general tire repair. Tire monitoring apparatus (not shown) may take the form of an annular assembly consisting of a circular antenna coupled to a transponder module. The module contains sensors that can measure various tire parameters such as pressure and temperature and communicate measured date to a remote receiver by means of the antenna. Other tire monitoring apparatus consist of a patch that attaches to the liner and likewise carries sensor electronics and communication means for accomplishing the desired task of monitoring the status of the tire air cavity. In other applications, for the purpose of repair of the tire, it may be necessary to attach a patch to the tire liner 28.

In the aforementioned applications and other applications known to those in the industry, attachment of a patch or tire monitoring apparatus to a tire liner 28 is effected by the use of an adhesive of known type and availability such as, but not limited to, epoxies. As described above, the presence of mold release agents to the surface of the liner 28 my act to impede the achievement of a proper bond between a tire monitoring apparatus or render such an attachment inconsistent or unpredictable. Hence, it may be necessary to remove the mold release agents from a portion of the tire liner, thus creating a target region 30 on the liner surface. The target region 30 may be located at various positions on the liner 28 depending upon the application. For example, a patch may be deployed in the crown area of the inner liner or along the sidewalls as required.

An annular antenna and transponder assembly is commonly attached to the inner liner 28 at a lower portion of the sidewall. The target region 30 for such an application therefore comprises an annular region surrounding the sidewall a nominal distance above the bead 22. Should cleansing be necessary to rid such a region of agents that inhibit adhesive bonding, the target region 30 must undergo a cleaning operation until the region is satisfactorily cleansed. Such an operation is time consuming and adds manufacturing cost. It is, accordingly, desirable to measure the adhesive capability of the target region 30 during or after the cleaning procedure to ascertain when a suitable level of adhesion capability is achieved. In measuring adhesion capability of the target surface 30, the cleaning cycle may be controlled with precision to render the optimum level of surface preparation.

The subject invention thus provides a means for measuring adhesion capability before applying an adhesive to the target surface 28 as a way to determine if the tire monitoring apparatus or patch will stick to the surface. Such a test may be a screen or an SPC test (i.e., Xbar-R chart), or may be an in-line inspection of every tire. Measuring adhesion capability may be used to control the installation or cleaning process or cause the tire to be rejected in the installation process as well.

Figure 4:
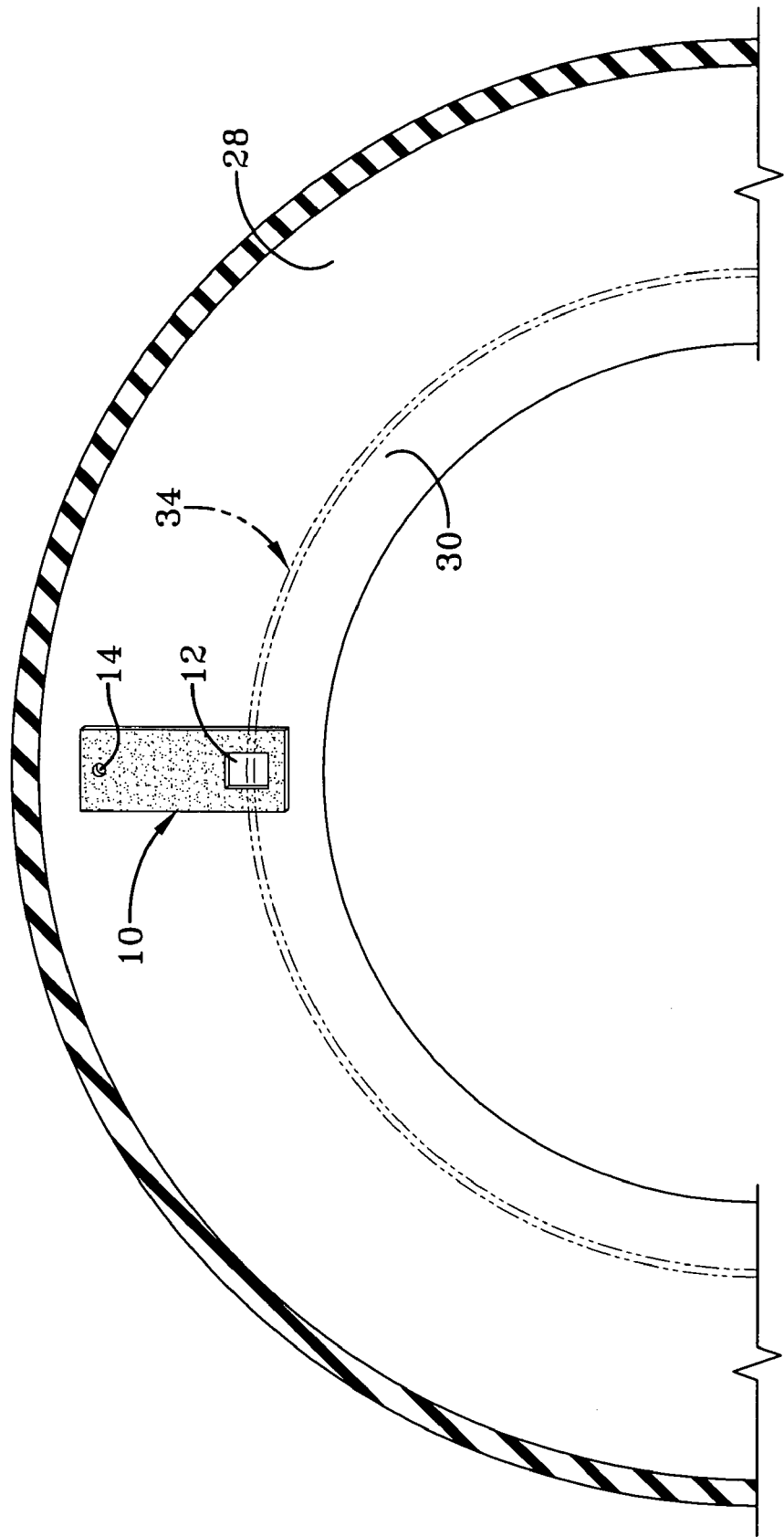
FIG. 4 is a section view through a tire portion showing positionment of the film strip relative to a target region of the tire liner.
Figure 5:
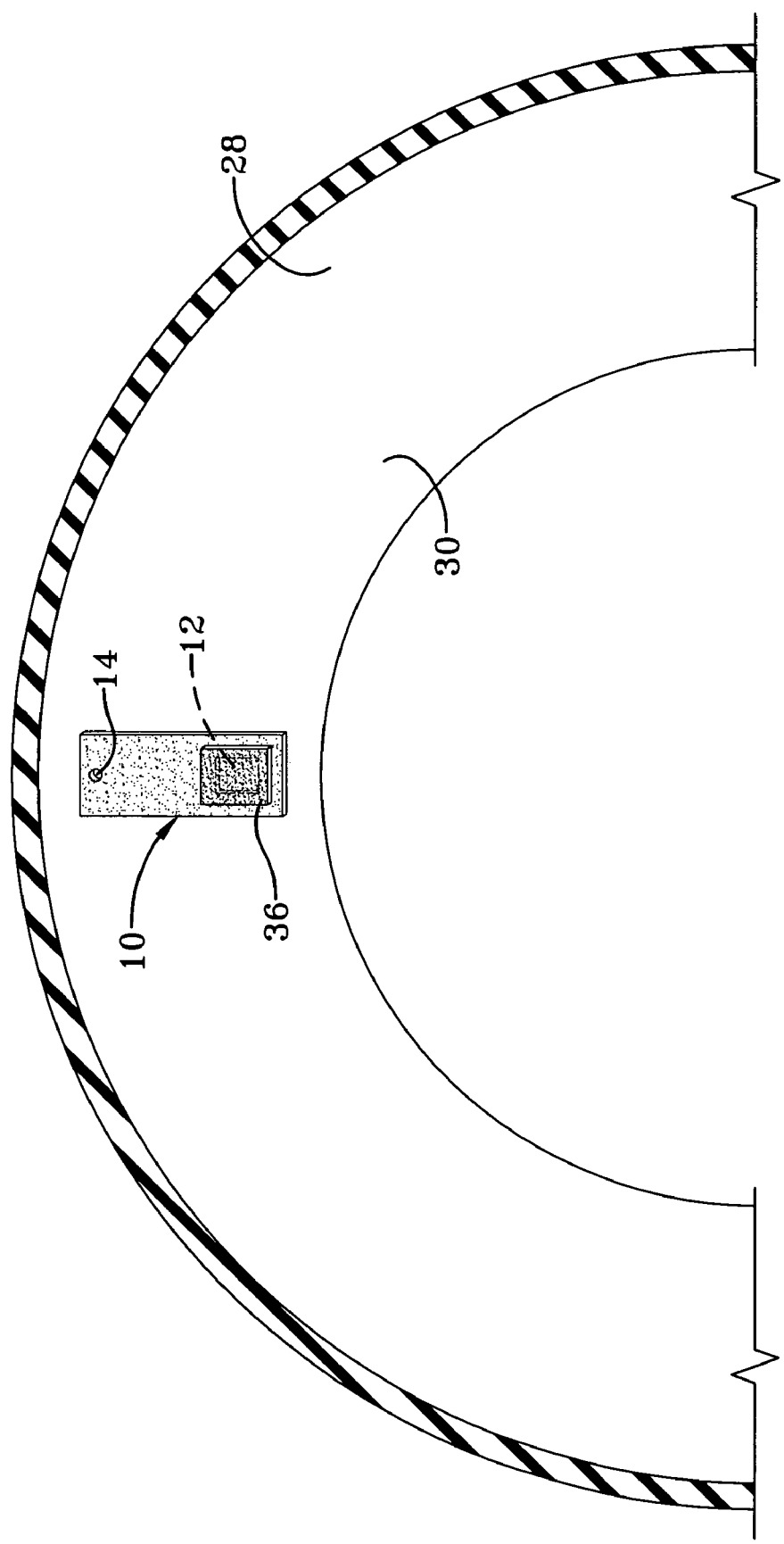
FIG. 5 is a section view through a tire portion showing the tape member covering the film strip opening prior to removal of the film strip.
Figure 6:
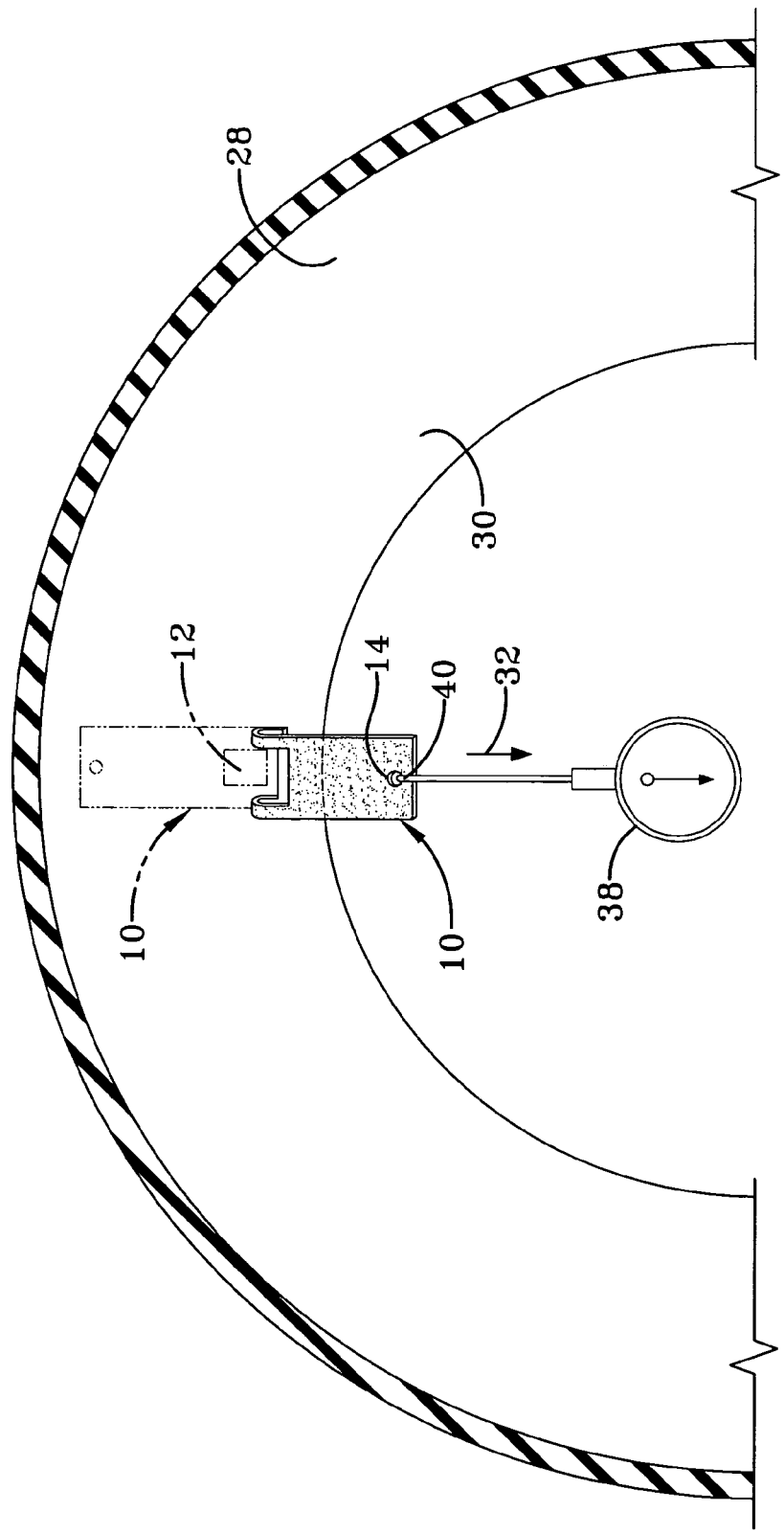
FIG. 6 is a section view through a tire portion showing removal of the film strip from the liner target region.

An annular tire monitoring apparatus 34 is shown in FIGS. 3, 4, and 5 for the purpose of illustration although the invention may used in other applications as described above. The film strip 10 is positioned on the liner 28 so that the cut-out opening 12 is over the target region 30 where the annular antenna is to be installed. By way of example without intent to limit the invention, a 3 by 8 inch strip of film having a one-inch square opening may be used. The strip 10 is preferably composed of material having low elongation when subjected to tensile forces. Thereafter, an adhesive backed tape layer 36 is attached over the film strip 10 covering opening 12 and is firmly pressed against the tire liner surface 30 through opening 12. The time and level of pressure is standardized to control the test parameters. By way of example, the tape may be pressed for one minute with a one kg weight. The tape adheres to the target surface 30 as a result.

The test proceeds as a scale 38 is attached to the film strip by means of a hook 40 attaching through a cable to the interface hole 14. Any slack in the cable is removed and the film strip 10 is folded back by directionally pulling the scale along line 32 as shown. As the film is peeled back and tape 36 removed from the liner 28, the peel force is measured by scale 38.

Through empirical trial, the measured force required to peel the film strip 10 and tape 36 from the target surface 30 is correlated with the adhesion capability of the surface. Such a correlation allows the cleanliness of the target surface to be ascertained as explained previously.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. Apparatus for measuring adhesion capability in a tire liner, characterized by:
   a film strip having a through opening and an attachment interface distanced from the opening;
   an adhesive backed cover member for attachment to the film strip in covering relationship to the strip opening;
   means attached to the strip attachment interface for exerting a directional peeling force upon the strip; and
   means for measuring the directional peeling force.

2. Apparatus according to claim 1 wherein the film strip opening is shaped and dimensioned to overlap at least part of a target region of a tire inner liner.

3. Apparatus according to claim 1 wherein the attachment interface comprises a through-hole.

4. Apparatus according to claim 1 wherein the cover member comprises a tape strip for attachment over the film strip and having an adhesive tape surface exposed through the film strip opening.

5. In combination a tire and apparatus for measuring adhesion capability of a tire inner liner characterized by:
   the tire liner having a target surface region;
   a film strip for attachment to the tire liner and having a through opening located for overlapping at least a portion of the tire liner target surface region and the film strip having an attachment interface distanced from the opening;
   an adhesive backed cover member for attachment to the film strip in covering relationship to the strip opening and the cover member including a portion for establishing adhesive contact with at least of portion of the tire liner target surface region through the film strip opening;
   means attached to the strip attachment interface for exerting a directional peeling force upon the strip sufficient to separate the cover member portion from the tire liner target surface region portion; and
   means for measuring the directional peeling force.

6. Apparatus according to claim 5, wherein the film strip opening is shaped and dimensioned to overlap at least part of a target region of a tire inner liner.

7. Apparatus according to claim 5, wherein the attachment interface comprises a through-hole.

8. Apparatus according to claim 5, wherein the cover member comprises a tape strip for attachment over the film strip and having an adhesive tape surface portion exposed through the film strip opening.

9. Apparatus according to claim 5, wherein the tire liner target surface region is an annular surface extending about a sidewall portion of the tire liner.

10. A method for measuring adhesion capability in a tire liner, characterized by the steps:

a. positioning a film strip over a tire liner surface, the film strip having an opening disposed to overlap a liner target surface region and an attachment interface distanced from the film strip opening;

b. applying an adhesive backed tape to the film strip over the film strip opening and into an adhesive attachment with a portion of the tire liner target region located through the film strip opening;

c. engaging the film strip interface to unitarily peel the film strip and the tape from the liner surface; and d. measuring the force required to effect the peeling of the film strip and tape from the liner surface.

* * * * *